United States Patent
Bochkariov et al.

(10) Patent No.: US 6,383,749 B2
(45) Date of Patent: *May 7, 2002

(54) METHODS OF LABELING NUCLEIC ACIDS FOR USE IN ARRAY BASED HYBRIDIZATION ASSAYS

(75) Inventors: Dmitry E. Bochkariov, Mountain View; Alex Chenchik, Palo Alto, both of CA (US)

(73) Assignee: Clontech Laboratories, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/454,183

(22) Filed: Dec. 2, 1999

Related U.S. Application Data

(63) Continuation-in-part of application No. 09/424,175, filed as application No. PCT/US98/10561 on May 21, 1998, now abandoned.

(51) Int. Cl.$^7$ .......................... C12Q 1/68; C12P 19/34; C07H 21/03; C07H 21/04; C12N 15/70
(52) U.S. Cl. ................. 435/6; 435/91.2; 435/320.1; 536/23.1; 536/24.3
(58) Field of Search ................ 435/6, 91.2, 320.1; 536/23.1, 24.3

(56) References Cited

U.S. PATENT DOCUMENTS

| 4,886,741 A | * | 12/1989 | Schwartz ........................ 435/5 |
| 5,241,060 A | | 8/1993 | Engelhardt et al. ............ 536/27 |
| 5,268,486 A | | 12/1993 | Waggoner et al. .......... 544/212 |
| 5,684,142 A | | 11/1997 | Mishra et al. .............. 536/22.1 |
| 5,776,682 A | * | 7/1998 | First et al. ...................... 435/6 |

FOREIGN PATENT DOCUMENTS

WO     98/53103     11/1998

OTHER PUBLICATIONS

Folsom et al, "Detection of DNA targets with Biotinylated and fluoresceinated RNA probes", Anal. Biochem. 182:309–314, 1989.*

Stratagene Catalog, p. 39, 1988.*

Ehlers et al, "Differentiation of T cell lymphokine gene expression: the in vitro acquisition of T cell memory", J. Exp. Med. 173:25–36, Jan. 1991.*

Chu, Barbara C.F., et al., "Synthesis of an Amplifiable Reporter RNA for Bioassays," *Nucleic Acids Research* (1986) vol. 14, No. (14):5591–5603.

Gebeyehu, Gulilat, et al., "Novel Biotinylated Nucleotide—Analogs for Labeling and Colorimetric Detection of DNA," *Nucleic Acids Research* (1987) vol. 15, No. (11):4513–4535.

Griffor, Matthew C., et al., "Fluorescent In Situ Hybridization to Soybean Metaphase Chromosomes," *Plant Molecular Biology* (1991) vol. 17:101–109.

Langer, Pennina R., et al., "Enzymatic Synthesis of Biotin–Labeled Polynucleotides:Novel Nucleic Acid Affinity Probes," *Proc. Natl. Acad. Sci. USA* (Nov. 1981) vol. 78, No. 11:6633–6637.

Pinkel, D., et al., "Cytogenetic Analysis Using Quantitative, High–Sensitivity, Fluorescence Hybridization," *Proc. Natl. Acad. Sci. USA* (May 1986) vol. 83:2934–2938.

* cited by examiner

*Primary Examiner*—Jeffrey Fredman
(74) *Attorney, Agent, or Firm*—Bret E. Field; Bozicevic, Field & Francis

(57) ABSTRACT

Methods and kits are provided for labeling nucleic acids, e.g. for use in array based hybridization assays. In the subject methods, target nucleic acid is generated from an initial nucleic acid source, e.g. mRNA, where the target nucleic acid is characterized by having at least one reactive functionality that is not a moiety found on naturally occurring nucleic acids. Functionalized label is then conjugated to the target nucleic acid, either before or after it has been hybridized to array of nucleic acids stably associated with the surface of a solid support. The subject methods find use in a variety of array based hybridization assays, including differential expression assays.

20 Claims, No Drawings

METHODS OF LABELING NUCLEIC ACIDS FOR USE IN ARRAY BASED HYBRIDIZATION ASSAYS

CROSS-REFERENCE TO RELATED APPLICATIONS

This application is a continuation-in-part of application Ser. No. 09/424,175 filed Nov. 19, 1999 now abandoned, which application claims priority to application Ser. No. PCT/US98/10561 filed on May 21, 1998; which claims priority to application Ser. No. 09/053,375 filed on Mar. 31, 1998 and application Ser. No. 08/859,998 filed on May 21, 1997, now U.S. Pat. No. 5,994,076, the disclosures of which are herein incorporated by reference.

INTRODUCTION

1. Field of the Invention

The field of the invention is nucleic acid labeling, particularly labeling of nucleic acid targets for use in array based hybridization assays.

2. Background of the Invention

Nucleic acid arrays have become an increasingly important tool in the biotechnology industry and related fields. Nucleic acid arrays, in which a plurality of nucleic acids are deposited onto a solid support surface in the form of an array or pattern, find use in a variety of applications, including drug screening, nucleic acid sequencing, mutation analysis, and the like. One important use of nucleic acid arrays is in the analysis of differential gene expression, where the expression of genes in different cells, normally a cell of interest and a control, is compared and any discrepancies in expression are identified. In such assays, the presence of discrepancies indicates a difference in the classes of genes expressed in the cells being compared.

In many currently employed array based gene expression analysis protocols, differences in mRNA levels between two samples are detected and related to the expression level of different genes in the compared samples. Detection of different mRNA levels typically involves the steps of generating a target nucleic acid population that is representative of the mRNA population of the test sample. In other words, a population of target nucleic acids is generated where the population is indicative of the different mRNA levels that are originally present in the sample. The target nucleic acid population may be DNA or RNA and may have the sequence of the initial mRNA or the complement thereof. Following generation, the population of target nucleic acids is hybridized to an array of probe nucleic acids stably associated with the surface of a solid support. Since the sequence and location of each probe is known, any resultant hybridization complexes that form on the array surface between target and probe can be used to identify those genes that are expressed in the cell from which the initial mRNA sample was obtained. The intensity of the individual signals can also be used to at least semi-quantitatively determine the expression level of the detected genes. Since the methods require detection of target/probe complexes on the array surface, the target nucleic acids are generally labeled so that they can be detected.

In many embodiments, the target nucleic acids are labeled during their generation step. In other words, the targets that are generated from the initial sample are labeled targets. A number of different protocols have been developed for producing populations of the labeled target nucleic acids from an initial source. Such methods include: (a) those based on the use of labeled primer; (b) those based on the use of one or more labeled nucleotides; and the like. While the above approaches are effective in many situations, they are not perfect. For example, the spectrum of fluorescent labels that may be employed in protocols where labeled targets are generated from labeled nucleotide analogs is limited, as not all fluorescently tagged nucleotide analogs can be processed by enzymes, e.g. polymerases, that are employed in the labeled target generation step.

As such, there is continued interest in the development of new protocols for producing labeled target nucleic acids. Of particular interest would be the development of a protocol which is suitable for producing fluorescently labeled target nucleic acids, in which the fluorescent label is covalently bound to the nucleic acid, where the protocol provides for the use of a broader range of fluorescent labels that can be used in current protocols where fluorescently tagged nucleotide analogs are employed in target generation.

Relevant Literature

Patents of interest include: U.S. Pat. Nos. 5,684,142; 5,286,486 and 5,241,060. Other references of interest include: Chu et al., Nuc. Acids Res. (July 1986) 14:5591–5603; Gebeyehu et al., Nuc. Acids Res. (1987) 15:4513; Griffor et al.., Plant Mol. Biol. (July 1991) 17:101–109; Langer et al., Proc. Nat'l Acad. Sci. U.S.A. (1981) 78:6633; and Pinkel et al., Proc. Nat'l Acad. Sci. USA (May 1986) 83:2934-8. See also: Methods in Molecule Biology 28: Protocols for Nucleic Acid Analysis by Non-radioactive Probes (Isaac ed.)(Humana Press 1994); Hermanson, Bioconjugate Techniques (Academic Press, 1995); and Nonisotopic Probing, Blotting, and Sequencing (Kricka ed) Academic Press, 1995).

SUMMARY OF THE INVENTION

Methods and kits are provided for labeling nucleic acids, e.g. for use in array based hybridization assays. In the subject methods, a population of target nucleic acid is first generated from an initial nucleic acid source, e.g. mRNA, where each target nucleic acid in the population is characterized by having at least one reactive functionality that is not a moiety found on naturally occurring nucleic acids. Functionalized label is then conjugated to the target nucleic acid, either before or after it has been hybridized to the array of nucleic acids stably associated with the surface of a solid support. The subject methods find use in a variety of array based hybridization assays, including differential expression assays.

DEFINITIONS

The term "nucleic acid" as used herein means a polymer composed of nucleotides, e.g. naturally occurring deoxyribonucleotides or ribonucleotides, as well as synthetic mimetics thereof which are also capable of participating in sequence specific, Watson-Crick type hybridization reactions, such as is found in peptide nucleic acids, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "target nucleic acid" means a nucleic acid of interest in a sample being tested with an array, where by "of interest" is meant that the presence or absence of target in the sample provides useful information, e.g. unique and defining characteristics, about the genetic profile of the cell(s) from which the sample is prepared. As such, target nucleic acids are not housekeeping genes or other types of genes which are present in a number of diverse cell types and therefore the presence or absence of which does not provide characterizing information about a particular cell's genetic profile.

DESCRIPTION OF THE SPECIFIC EMBODIMENTS

Methods and kits for labeling target nucleic acids for use in array based hybridization assays are provided. In the subject methods, a population of target nucleic acid is first generated from an initial nucleic acid source, e.g. mRNA, where each target nucleic acid in the population is characterized by having at least one reactive functionality that is not a moiety found on naturally occurring nucleic acids. Functionalized label is then conjugated to the target nucleic acid, either before or after it has been hybridized to array of nucleic acids stably associated with the surface of a solid support. The subject methods find use in a variety of array based hybridization assays, including differential expression assays. In further describing the invention, the subject methods are discussed first in greater detail followed by a review of the provided kits for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

METHODS

As summarized above, the subject invention provides a method of labeling target nucleic acids in array based hybridization protocols. In the subject methods, the first step is to generate target nucleic acids from an initial nucleic acid source, where the target nucleic acids are modified so as to include at least one reactive functionality, which functionality is not present in naturally occurring nucleic acids. This initial target generation step is followed by a label conjugation step, in which functionalized label is contacted with the functionalized target under conditions sufficient to form a conjugate of the label and the nucleic acids. This conjugation step may occur before or after the hybridization of the target nucleic acids to the probe nucleic acids of an array. These steps are now described separately in greater detail.

Functionalized Target Generation

As mentioned above, the first step in the subject methods is the generation of a population of target nucleic acids. As the subject methods are particularly suitable for use in array based hybridization assays in which gene expression in a particular cell or cell type is of interest, the target nucleic acid population that is generated in this step is one that is representative of the gene expression profile of the initial cell or cell type of interest. In such methods, the first step in the subject methods is to obtain a sample of nucleic acids, usually RNAs (e.g. total RNAs or mRNAs), from a physiological source. The physiological source of RNAs is prokaryotic or eukaryotic, normally eukaryotic, with physiological sources of interest including sources derived from single celled organisms such as yeast and multicellular organisms, including plants and animals, particularly mammals, where the physiological sources from multicellular organisms may be derived from particular organs or tissues of the multicellular organism, or from isolated cells derived therefrom. In those embodiments where one is comparing gene expression in different cell or tissue types, the physiological sources may be different cells from different organisms of the same species, e.g. cells derived from different humans, or cells derived from the same human such that the cells share a common genome, where such cells will usually be from different tissue types, including normal and diseased tissue types, e.g. neoplastic, cell types. In obtaining the sample of RNAs to be analyzed from the physiological source from which it is derived, the physiological source may be subjected to a number of different processing steps, where such processing steps might include tissue homogenation, nucleic acid extraction and the like, where such processing steps are known to the those of skill in the art. Methods of isolating RNA from cells, tissues, organs or whole organisms are known to those of skill in the art and are described in Maniatis et al., Molecular Cloning: A Laboratory Manual (Cold Spring Harbor Press)(1989).

The targets may be generated by any convenient method, where a variety of diverse and suitable methods are known in the art. A critical feature of any target generation method that is employed, however, is that the method results in the production of functionalized target, as described in greater detail below. Thus, mRNA can be functionalized and used directly as a target, e.g. via chemical or enzymatic modification to include the requisite reactive functionality. Alternatively, mRNA can be converted to a functionalized nucleic acid target, e.g. cDNA target, aRNA target, etc. In yet another embodiment, an excess of synthetic functionalized oligonucleotide target which is complementary to the probes on the array can be hybridized with the mRNA, followed by separation of any unbound target from the hybridized fraction. The hybridized fraction can then be hybridized to the array to reveal the expression pattern of the cellular source from which the mRNA was derived.

In many embodiments, methods for generating functionalized targets include the use of oligonucleotide primers and natural or functionalized nucleotides, e.g. ribonucleotides and deoxyribonucleotides (or dNTPs or rNTPs), in combination with one or more enzymatic activities, e.g. polymerases, reverse transcriptases, and the like, such that the functionalized targets are enzymatically generated. Primers that may be employed include oligo dT, random primers, e.g. random hexamers and gene specific primers, as described in PCT/US98/10561, the disclosure of which is herein incorporated by reference. In these embodiments, either primer or the nucleotides (or at least a portion thereof) are functionalized, such that functionalized target nucleic acids are produced. In many preferred embodiments, functionalized nucleotide analogs are employed in the enzymatic target generation step.

Of particular interest in the generation of labeled target is the use of a set of a representational number of gene specific primers, as described in U.S. patent application No. 08/859, 998, the disclosure of which is herein incorporated by reference. As the subject sets comprise a representational number of primers, the total number of different primers in any given set will be only a fraction of the total number of different or distinct RNAs in the sample, where the total number of primers in the set will generally not exceed 80%, usually will not exceed 50% and more usually will not 20% of the total number of distinct RNAs, usually the total number of distinct messenger RNAs (mRNAs), in the sample. Any two given RNAs in a sample will be considered distinct or different if they comprise a stretch of at least 100 nucleotides in length in which the sequence similarity is less than 98%, as measured using the FASTA algorithm at default settings. As the sets of gene specific primers comprise only a representational number of primers, with physiological sources comprising from 5,000 to 50,000 distinct RNAs, the number of different gene specific primers in the set of gene specific primers will typically range from about 20 to 10,000, usually from 50 to 2,000 and more usually from 75 to 15,000.

Each of the gene specific primers of the sets described above will be of sufficient length to specifically hybridize to a distinct nucleic acid member of the sample, e.g. RNA or cDNA, where the length of the gene specific primers will usually be at least 8 nt, more usually at least 20 nt and may be as long as 25 nt or longer, but will usually not exceed 50 nt. The gene specific primers will be sufficiently specific to hybridize to complementary template sequence during the generation of labeled nucleic acids under conditions sufficient for first strand cDNA synthesis, which conditions are known by those of skill in the art. The number of mismatches between the gene specific primer sequences and their complementary template sequences to which they hybridize during the generation of labeled nucleic acids in the subject methods will generally not exceed 20 number %, usually will not exceed 10 number % and more usually will not exceed 5 number %.

Generally, the sets of gene specific primers will comprise primers that correspond to at least 20, usually at least 50 and more usually at least 75 distinct genes as represented by distinct mRNAs in the sample, where the term "distinct" when used to describe genes is as defined above, where any two genes are considered distinct if they comprise a stretch of at least 100 nt in their RNA coding regions in which the sequence similarity does not exceed 98%, as determined using the FASTA algorithm at default settings.

By functionalized is meant that at least one reactive moiety is present on the compound, e.g. the primer or the nucleotide. Reactive moieties of interest are those that are capable of reacting with a corresponding reactive functionality present on another compound, e.g. label, to produce a covalent bond or linkage. In other words, reactive moieties of interest are those that can react with a second reactive moiety present on another compound, e.g. label, to produce a covalent bond or linkage between the first and second compounds, such that a conjugate of the first and second compounds is produced.

A critical limitation on the reactive moiety is that it must be one that is not found on naturally occurring nucleic acids, e.g. ribonucleic acids or deoxyribonucleic acids. For example, hydroxy groups are not reactive functionalities as that term is employed in herein, since they are present on naturally occurring nucleic acids. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono-or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the like. In the primers and nucleotides employed in the target generation step, the reactive functionality may be bonded directly to a nucleotide, or more typically, bonded to the nucleotide through a linking group. The linking group may vary, depending on whether the functionality is present on the primer or an individual nucleotide. For example, where the functional moiety is present on an individual nucleotide, it must be one that does not significantly impair the substrate specificity of the nucleotide, i.e. efficiency of using this functionalized nucleotide in comparison with a natural nucleotide. As such, those preferred embodiments where functionalized nucleotide analogs are employed in enzymatic target generation, the functional moiety and any linking are chosen so that they do not substantially impair the ability of the nucleotide to be used or incorporated by a polymerase. Representative linking groups include carbon containing linking groups, typically ranging from about 2 to 18, usually from about 2 to 8 carbon atoms, where the carbon containing lanking groups may or may not include one or more heteroatoms, e.g. S, O, N etc., and may or may not include one or more sites of unsaturation. Of particular interest in many embodiments are alkyl linking groups, typically lower alkyl linking groups of 1 to 6, usually 1 to 4 carbon atoms, where the linking groups may include one or more sites of unsaturation.

The functionalized nucleotides (or primers) used in the above methods of functionalized target generation may be fabricated using known protocols or purchased from commercial vendors, e.g. Sigman, Roche, RPI, NEN, Genosys, Operon, and the like. Specific nucleotide analogs of interest include amino modified nucleotide analogs, e.g. aminoallyl-dUTP, aminopropargyl-dATP, and the like.

This first step of functionalized target generation results in the production of a plurality of distinct, functionalized, target nucleic acids which are derived or copied from mRNA from the same cell or cell type and therefore are representative of the expression profile of that cell or cell type. Two target nucleic acids are considered to be distinct in a given population if their sequences are different. Depending on the protocol employed, e.g. whether oligo dT primers, random primers or gene specific primers were employed, the number of distinct target nucleic acids that is generated in a given target generation step may vary greatly. For a given initial eukaryotic mRNA source, the number of distinct target nucleic acids that is generated is generally at least about 100, usually at least about 500 and more usually at least about 1,000, where the number may be as great as 50,000 or greater, but generally does not exceed about 20,000 and usually does not exceed about 15,000. Common to each of the generated target nucleic acids will be the presence of at least one functional moiety, as described above, where the number of functional moieties on a given target may vary greatly depending on the protocol employed to generate the target, e.g. whether the functionalized primer or functionalized nucleotides were employed to generate the target. The number of functionalized moieties present in each target can be tailored in an appropriate fashion by selecting a specific amount of functionalized analog to be included in the enzymatic target generation step. Usually the number of functional moieties incorporated into the target nucleic acid is at least 1, commonly at least 1 moiety in 300 nucleotides, and more commonly at least 1 moiety in about 50 to 100 nucleotides, where the number generally does not exceed about 1 moiety in 10 nucleotides, so as to provide an efficiency of coupling with the functionalized label of at least about 30%, more commonly at least 50% and most commonly at least 70%.

Target Nucleic Acid Labeling

To detectably label the population of functionalized target nucleic acids, as described above, a population of conjugates of the functionalized target nucleic acids and detectable labels (either directly or indirectly detectable, preferably directly detectable) is produced. The population of conjugates may be produced before or after hybridization of the target nucleic acids to an array of probe nucleic acids, as described in greater detail infra. To produce the above mentioned target nucleic acid/label conjugates, i.e. labeled target nucleic acid, from the functionalized target nucleic acid produced in the first step, the functionalized target nucleic acid population is contacted with functionalized label under conditions sufficient for the functional moiety of the target nucleic acid to react with the corresponding functional moiety present on the label to produce a covalent bond between the label and the nucleic acid.

As such, functionalized labels employed in the subject methods include a functional moiety and a label moiety. The functional moiety of the functionalized labels may vary greatly, and is chosen in view of the functional moiety present on the functionalized target nucleic acid. In other words, the functional moiety present on the functionalized label must be one which reacts with the functional moiety present on the functionalized target nucleic acid to produce a covalent bond between the target nucleic acid and the label. In addition, the functional moiety should be one that does not react with a group present on a naturally occurring nucleic acid, such that the functional moiety reacts exclusively with the functional moiety present on the functionalized target. Representative functional moieties that may be present on the label include: amino, sulfhydryl, sulfoxyl, aminosulfhydryl, azido, epoxide, isothiocyanate, isocyanate, anhydride, monochlorotriazine, dichlorotriazine, mono-or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the like, where groups of particular interest that do not react with moieties present on naturally occurring nucleic acids are: N-hydroxysuccinimide groups, isothiocyanates, and the like.

The label component of the functionalized label may be directly or indirectly detectable, but is generally directly detectable. Examples of directly detectable labels include isotopic and fluorescent labels. Isotopic moieties or labels of interest include $^{32}P$, $^{33}P$, $^{35}S$, $^{125}I$, and the like. Fluorescent moieties or labels of interest include coumarin and its derivatives, e.g. 7-amino-4-methylcoumarin, aminocoumarin and hydroxycoumarin, BODIPY dyes, such as BODIPY FL, cascade blue, Cascade Yellow, fluorescein and its derivatives, e.g. fluorescein isothiocyanate, Oregon green, Marina Blue, rhodamine dyes, e.g. rhodamine red, tetramethylrhodamine and rhodamine 6G, Texas Red, eosins and erythrosins, cyanine dyes, e.g. Cy3 and Cy5, macrocyclic chelates of lanthanide ions, e.g. quantum dye™, fluorescent energy transfer dyes, such as thiazole orange-ethidium heterodimer, TOTAB, Alexa, etc. Labels can also be proteins with luminescent properties, e.g. green fluorescent protein, phicoerythrin, etc. Also of interest are particle labels, e.g. light scattering particles. Labels may also be members of a signal producing system that act in concert with one or more additional members of the same system to provide a detectable signal. Illustrative of such labels are members of a non-covalent specific binding pair, such as ligands, e.g. biotin, fluorescein, digoxigenin, other haptens, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic or fluorescent product or a product that emits light, e.g. alkaline phosphatase conjugate antibody, luciferase, horseradish peroxidase; and the like. In many embodiments, however, the label is a fluorescent label which is modified to include a functional moiety, as described above.

In certain preferred embodiments, the functional group present on the functionalized target nucleic acid is an amino group. In such embodiments, of particular interest is the use of a N-hydroxysuccinimide ester functionalized label of the following structure:

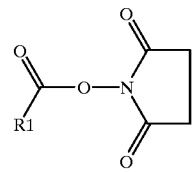

where R1 is the label moiety, and preferably a fluorescent moiety. Specific fluorescent moieties that may be R1 include: cyanine dyes, e.g. Cy3, Cy5; Alexa dyes, e.g. Alexa Fluor 532; BODIPY dyes, hydroxycoumarin, Cascade Blue, fluorescein, Oregon Green, rhodamine 6G, and the like.

Structures of representative N-hydroxysuccinimide ester functionalized dyes are as follows:

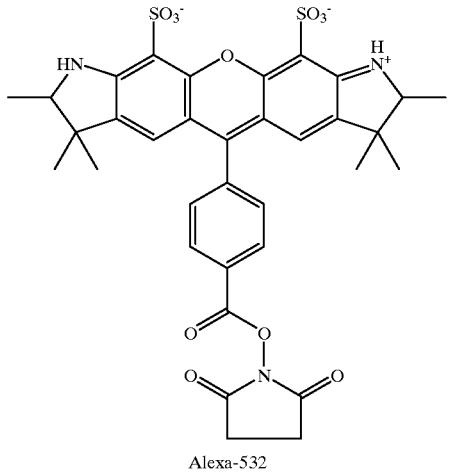

Alexa-532

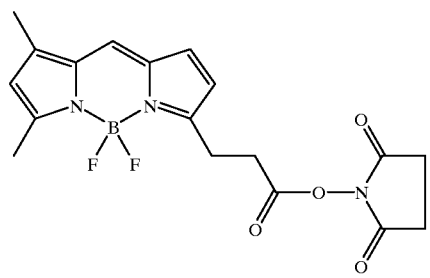

BODIPY-FL

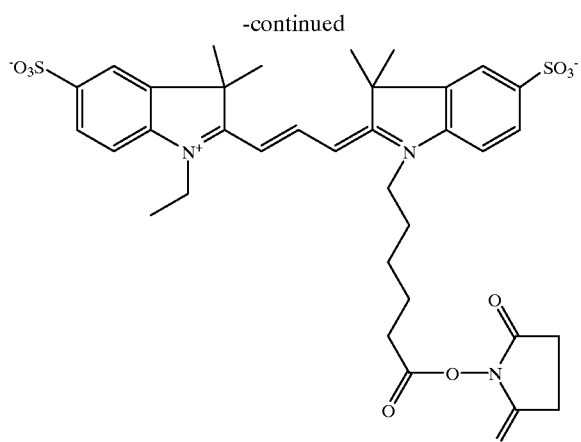

Cy3

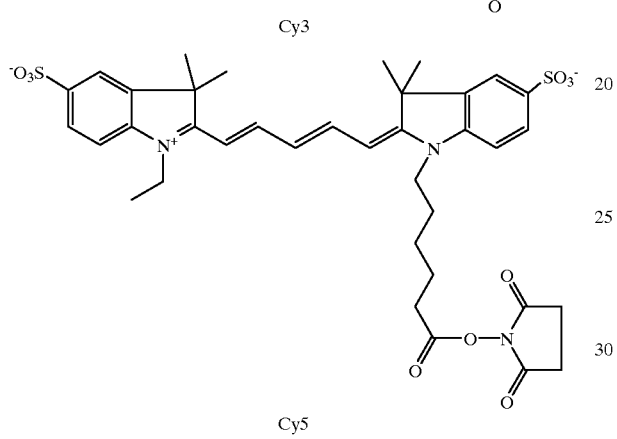

Cy5

The above described functionalized labels may be fabricated using any convenient protocol or purchased from commercial vendors. Representative protocols for fabricating functionalized labels are disclosed in U.S. Pat. Nos. 4,404,289; 4,405,711; 4,337,063 and 5,268,486; as well as Br. Pat. No. 1,529,202; the disclosures of which are herein incorporated by reference.

As mentioned above, the functionalized label is contacted with the functionalized target under conditions sufficient for conjugation of the label to the target to occur, i.e. for the target and reactive functionalities to react with each other to produce a covalent bond or linkage between the label and the nucleic acid. The particular conditions during contact will depend, at least in part, on the nature of the first and second functionalities on the target nucleic acid and label, respectively. For example, where the first functionality present on the target is an amino group and the second functionality present on the label is an N-hydroxysuccinimide ester group, the contact conditions are chosen such that a reaction occurs between the amino and N-hydroxysuccinimide ester groups to form a covalent bond between the label and the nucleic acid. In this specific preferred embodiment, representative conditions may or may not include the presence of an organic base, such as triethylamine, diisopropylethylamine, N-methylmorpholine, pyridine or 1,8-diazabicyclo-undec-7-ene (DBU), and the like and a suitable solvent, such as N,N-dimethylformamide, dimethylsulfoxide, ethyl acetate, dioxane, tetrahydrofuran, dichloromethane, 1,2-dichloroethane, chloroform, carbon tetrachloride, N-methylpyrrolidone, pyridine, etc., or a mixture thereof. Optional additives include 4-dimethylaminopyridine (DMAP), 1-hydroxybenzotriazole (HOBt), 1-hydroxy-7-azabenzotriazole (HOAt), O-benzotriazol-1-yl-tetramethyluronium hexaflourophosphate (HBTU), and the like. As the presence of water is desirable to keep the nucleic acid target in solution, the presence of buffer component is required to maintain the pH levels at an appropriate value. pH value depends on the functional groups used, organic solvents present in the reaction and can be determined by those of skill in the art. Buffer components of interest include: phosphate, MOPS, HEPES, CAPS, etc. The reaction is typically conducted at temperatures ranging from $-20°$ C. to $100°$ C., preferably from $0°$ C. to $50°$ C. One of skill in the art may determine the appropriate concentrations of the reagents and the duration of the reaction.

The following schematic provides a representation of the conjugation reaction between a succinimide modified label and a amino modified target nucleic acid (R1 is the label):

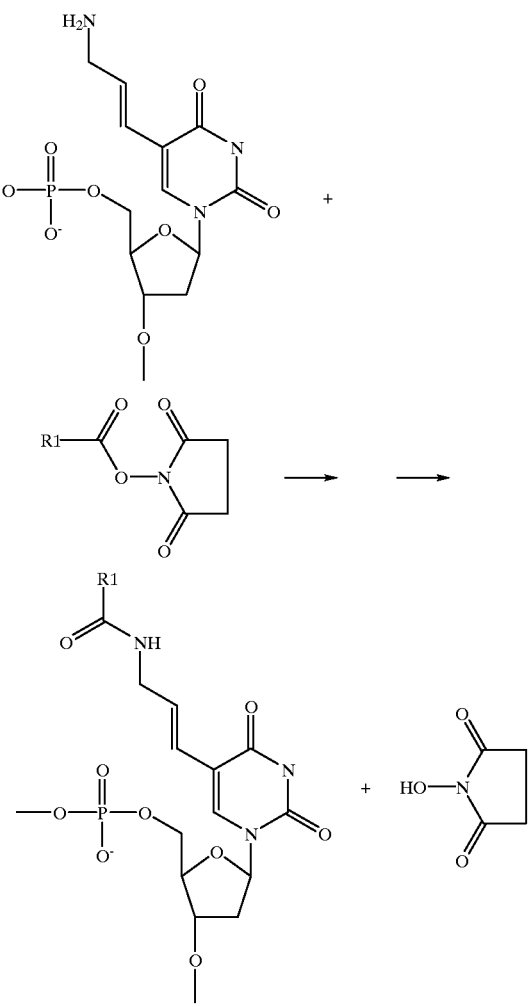

The above conjugation step results in the production of a population of labeled target nucleic acids. As mentioned above, the above conjugation step may be performed either before or after the population of target nucleic acids is hybridized to an array of probe nucleic acids. Therefore, in certain embodiments hybridization occurs after the above conjugation step, such that labeled target is hybridized to the array. In other preferred embodiments, the target is hybridized to the array prior to conjugation with the functionalized label, such that non-labeled but functionalized target is hybridized to the array followed by conjugation of the hybridized functionalized target to the label.

Array Hybridization

As mentioned above, the above conjugation step between the functionalized label and the functionalized target may occur before or after the target has been hybridized to an array of probe nucleic acids stably associated with the surface of a solid support, where in certain preferred embodiments hybridization occurs prior to conjugation. A variety of different array devices in which a plurality of distinct nucleic acid probes are stably associated with the surface of a solid support are known to those of skill in the art. Such arrays may vary in a number of different ways, including average probe size, sequence or types of probes, nature of bond between the probe and the array surface, e.g. covalent or non-covalent, and the like. The labeling protocol of the present invention is not limited in its utility to any specific type of array, but may be used with a variety of different types of arrays. Representative arrays with which the subject labeling protocol may be employed include those described in: U.S. Pat. Nos. 5,143,854; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,503,980; 5,510,270; 5,525,464; 5,527,681; 5,529,756; 5,545,531; 5,547,839; 5,554,501; 5,556,752; 5,561,071; 5,580,726; 5,580,732; 5,599,695; 5,599,672; 5,610;287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; WO 93/17126; WO 95/11995; WO 95/21265; WO 95/21944; WO 95/35505; WO 96/31622; WO 97/10365; WO 97/27317; WO 99/35505; EP 373 203; EP 785 280; EP 799 897 and UK 8 803 000, as well as those described in U.S. Patent Application Serial Nos. 08/859,998; 09/225,928; 09/225,201; 09/053,375; 09/221,480; 09/222,432; 09/222,436; 09/222,437; 09/222,251; 09/221,481; 09/222,256; 09/222,253; 09/003,723; 09/269,586; 60/104,179; 09/298,361; 09/440,829 entitled Long Oligonucleotide Arrays (Attorney Docket Number CLON-015) and PCT/US98/10561; the disclosures of which are herein incorporated by reference.

During hybridization, the population of target nucleic acids is contacted with the array under hybridization conditions, where such conditions can be adjusted, as desired, to provide for an optimum level of specificity in view of the particular assay being performed. Suitable hybridization conditions are well known to those of skill in the art and reviewed in Maniatis et al, supra and WO 95/21944. Of particular interest in many embodiments is the use of stringent conditions during hybridization. Stringent conditions are known to those of skill in the art.

Where one is using the subject labeling methods in applications for analyzing the differences in the population of target nucleic acids generated from two or more physiological sources using the arrays described above, in certain embodiments each population of target nucleic acids are separately contacted to identical probe arrays or together if they are labeled by distinguishable labels to the same array under conditions of hybridization, preferably under stringent hybridization conditions, such that target nucleic acids hybridize to complementary probes on the substrate surface. In yet other embodiments, the target nucleic acids are combined with a distinguishably labeled standard or control target nucleic acids followed by hybridization of the combined populations to the array surface, as described in application Ser. No. 09/298,361; the disclosure of which is herein incorporated by reference.

Where all of the target sequences are detected using the same label, different arrays will be employed for each physiological source (where different could include using the same array at different times). Alternatively, where the labels to be employed for the different target populations are different and distinguishable for each of the different physiological sources being assayed, the opportunity arises to use the same array at the same time for each of the different target populations. Examples of distinguishable labels are well known in the art and include: two or more different emission wavelength fluorescent dyes, like Cy3 and Cy5, combination of fluorescent proteins and dyes, like phicoerythrin and Cy5, two or more isotopes with different energy of emission, like $^{32}P$ and $^{33}P$, gold or silver particles with different scattering spectra, labels which generate signals under different treatment conditions, like temperature, pH, treatment by additional chemical agents, etc., or generate signals at different time points after treatment. Using one or more enzymes for signal generation allows for the use of an even greater variety of distinguishable labels, based on different substrate specificity of enzymes (alkaline phosphatase/peroxidase).

The subject labeling protocols may be tailored depending on when the target is to be hybridized to the probe array. For example, where the target populations are to be hybridized to the probe array after hybridization, one can use the same functional moiety pairs for producing the labeled target nucleic acids. For instance, one can produce a first labeled target nucleic acid population from amino modified target nucleic acid and N-hydroxysuccinimide ester modified Cy3. The second distinguishably labeled target nucleic acid population can then be produced separately from amino modified target nucleic acid and N-hydroxysuccinimide ester modified Cy5. The two separately prepared and distinguishably labeled populations are then combined and hybridized to the surface of the same array. In other embodiments where the functionalized label is contacted with the functionalized target following target hybridization, the functionalized moiety pairs chosen for the first and second sets of target nucleic acid and label are different and non cross-reactive, such that functionalized first label exclusively conjugates to the first hybridized target population while functionalized second label exclusively conjugates to the second hybridized target population. For example, a first target population may be amino modified for conjugation to N-hydroxysuccinimide ester modified label and a second target population may be sulfhydryl modified for conjugation to an iodoacetyl or maleimide modified second label.

Following hybridization, non-hybridized target nucleic acid is removed from the support surface (usually prior to conjugation with label in those embodiments where conjugation occurs following hybridization), conveniently by washing, generating a pattern of hybridized nucleic acid on the substrate surface. A variety of wash solutions are known to those of skill in the art and may be used.

The above steps result in the production of hybridization patterns of labeled target nucleic acid on the array surface. The resultant hybridization patterns of labeled nucleic acids may be visualized or detected in a variety of ways, with the particular manner of detection being chosen based on the particular label of the target nucleic acid, where representative detection means include scintillation counting, autoradiography, fluorescence measurement, colorimetric measurement, light emission measurement, light scattering, and the like.

Following detection or visualization, the hybridization patterns may be compared to identify differences between the patterns. Where arrays in which each of the different probes corresponds to a known gene are employed, any discrepancies can be related to a differential expression of a particular gene in the physiological sources being compared.

UTILITY

The subject methods of labeling target nucleic acids in array based hybridization assays find use in, among other applications, differential gene expression assays. Thus, one may use the subject methods in the differential expression analysis of: (a) diseased and normal tissue, e.g. neoplastic and normal tissue, (b) different tissue or tissue types; (c) developmental stage; (d) response to external or internal stimulus; (e) response to treatment; and the like. The subject arrays therefore find use in broad scale expression screening for drug discovery, diagnostics and research, as well as studying the effect of a particular active agent on the expression pattern of genes in a particular cell, where such information can be used to reveal drug toxicity, carcinogenicity, etc., environmental monitoring, disease research and the like.

KITS

Also provided are kits for use in preparing labeled target nucleic acid for use in hybridization assays, e.g. differential gene expression analysis assays. Such kits according to the subject invention will at least comprise a means for generating functionalized target and at least one functionalized label. The means for generating functionalized label may vary, where representative means may be functionalized primers, functionalized nucleotides, e.g. dNTPs, rNTPs and the like. The kits may further comprise one or more additional reagents employed in the various methods, such as primers for generating target nucleic acids, dNTPs and/or rNTPs, which may be either premixed or separate, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g streptavidin-alkaline phosphatase conjugate, chemifluorescent or chemiluminescent substrate, and the like.

The following examples are offered by way of illustration and not by way of limitation.

EXPERIMENTAL

Example 1

Preparation of Cy3 labeled target nucleic acid.

1. To 5 μg of polyA+ placental RNA add 5 μl of gene specific primers (0.2 μM each as described in PCT/US98/10561 the disclosure of which is herein incorporated by reference). Add water to total final volume of 25 μl.
2. Heat at 70° C. for 5 min.
3. Cool to 48° C., add 25 μl of following master mix:

| 5 × first strand buffer | 10 μl |
|---|---|
| 10 × dNTP mixture | 5 μl |
| MMLV RT (200 u/ml) | 2.5 μl |
| Milli Q water | 7.5 μl |

| Composition of 10 × dNTP mixture for 100 μl | | | |
|---|---|---|---|
| Reagent | Stock conc. | Amount | Final conc. |
| DATP | 100 mM | 5 μl | 5 mM |
| DCTP | 100 mM | 5 μl | 5 mM |
| DGTP | 100 mM | 5 μl | 5 mM |
| DTTP | 100 mM | 2.5 μl | 2.5 mM |
| Allylamino-dUTP | 10 mM | 25 μl | 2.5 mM |
| Milli Q water | | 57.5 μl | |

4. Incubate at 48° C. for 30 min.
5. Heat to 70° C. for 5 min.
6. Cool to 37° C. and add 0.5 μl of RNase H (10 U/μl)
7. Incubate at 37° C. for 15 min.
8. Add 0.5 μl of 0.5 M EDTA pH 8.0 (to make final concentration of EDTA 5 mM).
9. Add 5 μl of QuickClean resin, vortex ~1 min.
10. Apply the sample onto the SPIN −X centrifuge tube filter.
11. Centrifuge at maximum speed for 1 min.
12. Add 5.5 μl of 3M Sodium Acetate pH 5.2, vortex and then add 137.5 μl 100% ETOH.
13. Freeze at −20° C. for approximately 1 hr.
14. Spin at maximum speed for 20 min.
15. Wash pellets with 70% ETOH.
16. Dissolve the cDNA pellet in 10 μl of 0.1M CAPS-Na, pH 10.5.
17. Add 45 μl DMSO (quality of DMSO is the most important issue for this procedure; use only DMSO that is provided) into a tube with Cy3 mono-functional reactive dye (Cy3 N-hydroxysuccinimide ester), vortex and spin down.
18. Add 10 μl of Cy3-reactive dye/DMSO solution to 10 μl of the cDNA solution from step 16, mix well and leave the tube with the reaction mixture at room temperature in the dark place or wrapped with aluminum foil for 30 min.
19. Add 2 μl of 3M Sodium Acetate pH 5.2, vortex and then add 50 μl of 100% ETOH.
20. Freeze at −20° C. for 1 to 3 hrs.
21. Spin down at maximum speed for 20 min.
22. Wash pellets with 70% ETOH.
23. Dissolve in 50 μl of water.
24. Purify using Nucleospin column, according to the protocol, but wash column 3 times with ethanol instead of 1 time as in handbook. Elute with 50 μl of water.
25. Take O.D./record spectrum (as the amount of cDNA generated is very small, O.D. measurement is optional depending on the sensitivity of a spectrophotometer available). Ratio 260/550 should generally be in range from 3 to 10.

Cy3 labeled target nucleic acid prepared as described above is then suitable for use in array based hybridization assays.

Example 2

Post Hybridization Labeling

Target nucleic acids are prepared as described above, except that the amino functional group is replaced with an SH group. The target nucleic acids are then hybridized to an array of probe nucleic acids. Following hybridization, the array surface is washed to removed unhybridized target. The array surface is then contacted with a solution of maleimide functionalized label under conditions sufficient for the functionalized label to conjugate to the hybridized target via the SH moiety, resulting in an array of labeled hybridized targets.

It is evident that the subject invention provides an important new method for generating labeled target nucleic acids for use in array based hybridization assays. With the subject methods, one is not limited to using labeled analogs that can be processed by polymerases, since the labeling step occurs after the target generation step. As such, the number of different types of labels that can now be used in array based hybridization assays, including the number of different types of fluorescent labels, is greatly increased. As such, the subject invention represents and important contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing a population of labeled target nucleic acids, said method comprising:

generating a population of target nucleic acids comprising a first reactive functionality, wherein said first reactive functionality is a moiety that is not present on naturally occurring nucleic acids and said population of target nucleic acids is generated by contacting an initial mRNA sample with a fluid composition of at least 50 distinct gene specific primers under conditions sufficient to enzymatically generate said population of target nucleic acids, wherein each constituent distinct gene specific primer of said fluid composition has a nucleotide sequence that is complementary to a distinct mRNA and wherein each target nucleic acid is generated using a single gene specific primer; and contacting said population of nucleic acids with a functionalized label comprising a second reactive functionality under conditions sufficient for said first and second reactive functionalities to react with each other to produce a covalent bond between said label and said nucleic acid to produce said population of labeled target nucleic acids.

2. The method according to claim 1, wherein said label is a directly detectable label.

3. The method according to claim 2, wherein said label is a fluorescent label.

4. The method according to claim 1, wherein said population of target nucleic acids is enzymatically generated.

5. The method according to claim 4, wherein at least one nucleotide functionalized with said first functionality is employed in said generating step.

6. A method of hybridizing a population of target nucleic acids to an array made up of a plurality of probe nucleic acids stably associated with the surface of a solid support, said method comprising:

generating said population of target nucleic acids by contacting an initial mRNA sample with a fluid composition of at least 50 distinct gene specific primers under conditions sufficient to enzymatically generate said population of target nucleic acids, wherein each constituent distinct gene specific primer of said fluid composition has a nucleotide sequence that is complementary to a distinct mRNA and wherein each target nucleic acid is generated using a single gene specific primer, wherein each constituent target nucleic acid comprises a first reactive functionality, wherein said first reactive functionality is a moiety that is not present on naturally occurring nucleic acids; and hybridizing said generated population of target nucleic acids to said array;

with the proviso that said method further comprises a step of conjugating a functionalized label comprising a second reactive functionality to said population of target nucleic acids by a reaction between said first and second reactive functionalities.

7. The method according to claim 6, wherein said conjugating occurs prior to said hybridizing.

8. The method according to claim 6, wherein said conjugating occurs after said hybridizing.

9. The method according to claim 6, wherein said first reactive functionality is selected from the group consisting of amino, sulfhydryl, azido, isothiocyanate and sulfoxyl.

10. The method according to claim 6, wherein said second reactive functionality is an N-hydroxysuccinimide ester moiety.

11. The method according to claim 6, wherein said label is directly detectable.

12. The method according to claim 11, wherein said label is a fluorescent label.

13. The method according to claim 6, wherein said population of target nucleic acids is enzymatically generated.

14. An array based hybridization method, said method comprising:

enzymatically generating a plurality of amino modified distinct target nucleic acids from an initial RNA source by contacting said initial mRNA source with a fluid composition of at least 50 distinct gene specific primers under conditions sufficient to enzymatically generate said population of target nucleic acids, wherein each constituent distinct gene specific primer of said fluid composition has a nucleotide sequence that is complementary to a distinct mRNA and wherein each target nucleic acid is generated using a single gene specific primer;

contacting N-hydroxysuccinimide ester functionalized label with said plurality of amino modified distinct target nucleic acids under conditions sufficient to produce a plurality of labeled target nucleic acid conjugates; and hybridizing said plurality of labeled target nucleic acid conjugates to an array of a plurality of distinct nucleic acid probes stably associated with the surface of a solid support.

15. The method according to claim 14, wherein said label is a fluorescent label.

16. An array based hybridization method, said method comprising:

(a) enzymatically generating a plurality of amino modified distinct target nucleic acids from an initial nucleic acid source by contacting an initial mRNA sample with a fluid composition of at least 50 distinct gene specific primers under conditions sufficient to enzymatically generate said population of target nucleic acids, wherein each constituent distinct gene specific primer of said fluid composition has a nucleotide sequence that is complementary to a distinct mRNA and wherein each target nucleic acid is generated using a single gene specific primer;

(b) hybridizing said plurality of amino modified target nucleic acid conjugates to an array of a plurality of distinct nucleic acid probes stably associated with the surface of a solid support to produce at least one duplex of an amino modified target nucleic acid and a probe nucleic acid on said surface of said array; and (c) contacting N-hydroxysuccinimide ester functionalized label with said surface of said array under conditions sufficient for said label to conjugate to said amino modified target nucleic acid.

17. The method according to claim 16, wherein said label is a fluorescent label.

18. The array produced according to claim 6.

19. A kit for use in labeling a nucleic acid, said kit comprising:

(a) nucleotides;

(b) functionalized nucleotide analogs comprising a first reactive functionality not present in naturally occurring nucleic acids;

(c) functionalized label comprising a second reactive functionality, wherein said second reactive functionality is capable of reacting with said first reactive functionality; and (d) a fluid composition of at least 50 distinct gene specific primers wherein each constituent distinct gene specific primer of said fluid composition has a nucleotide sequence that is complementary to a distinct mRNA.

20. The kit according to claim 19, wherein said kit further comprises an array of a plurality of probes stably associated with the surface of a solid support.

* * * * *